United States Patent
Zhang et al.

(10) Patent No.: US 11,182,925 B2
(45) Date of Patent: Nov. 23, 2021

(54) METHOD OF DETERMINING A CORRESPONDENCE BETWEEN FRAMES OF MEDICAL IMAGE DATA WITH AND WITHOUT CONTRAST MEDIUM THROUGH PROBABILITY DISTRIBUTION MAPS RELATING TO POSITION OF A FEATURE

(71) Applicant: Siemens Healthcare GmbH, Erlangen (DE)

(72) Inventors: Liheng Zhang, Orlando, FL (US); Vivek Kumar Singh, Princeton, NJ (US); Kai Ma, Princeton, NJ (US); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 395 days.

(21) Appl. No.: 16/174,324

(22) Filed: Oct. 30, 2018

(65) Prior Publication Data
US 2019/0139259 A1      May 9, 2019

Related U.S. Application Data

(60) Provisional application No. 62/581,983, filed on Nov. 6, 2017.

(30) Foreign Application Priority Data

Jun. 15, 2018 (EP) ..................................... 18177904

(51) Int. Cl.
*G06T 7/73* (2017.01)
*A61B 5/00* (2006.01)
(Continued)

(52) U.S. Cl.
CPC ................ *G06T 7/74* (2017.01); *A61B 5/064* (2013.01); *A61B 5/7264* (2013.01); *A61B 90/37* (2016.02);
(Continued)

(58) Field of Classification Search
CPC ... G06T 7/74; G06T 7/11; G06T 11/60; G06T 2207/10081; G06T 2207/10088;
(Continued)

(56) References Cited

U.S. PATENT DOCUMENTS

2008/0275335 A1* 11/2008 Zhang ...................... A61B 6/12
600/424
2014/0094691 A1     4/2014 Steinberg et al.
(Continued)

FOREIGN PATENT DOCUMENTS

EP           3142558 A1     3/2017
WO     2015173821 A1    11/2015
(Continued)

OTHER PUBLICATIONS

Xiang L, Qiao Y, Nie D, An L, Wang Q, Shen D. Deep auto-context convolutional neural networks for standard-dose PET image estimation from low-dose PET/MRI. Neurocomputing. 2017;267:406-416. (Year: 2017).*

(Continued)

*Primary Examiner* — Serkan Akar
*Assistant Examiner* — Richmond J Van Winter (57) ABSTRACT

A correspondence between frames of a set of medical image data is determined where the set of medical image data includes at least one frame acquired without contrast medium and at least one frame acquired with contrast medium. First data representing a first image frame acquired without contrast medium is received. Second data representing a second image frame acquired with contrast medium is received. A position of a feature of a medical device in the second image frame is determined at least partly on the basis of a position of the feature determined from the first image frame.

6 Claims, 7 Drawing Sheets

(51) Int. Cl.
*G06T 11/60* (2006.01)
*A61B 90/00* (2016.01)
*A61B 5/06* (2006.01)
*A61F 2/82* (2013.01)
*A61M 25/10* (2013.01)

(52) U.S. Cl.
CPC .............. *A61F 2/82* (2013.01); *A61M 25/104* (2013.01); *G06T 11/60* (2013.01); *A61B 2090/364* (2016.02); *A61B 2090/3966* (2016.02); *A61B 2090/3983* (2016.02); *A61F 2250/0098* (2013.01); *G06T 2207/10081* (2013.01); *G06T 2207/10088* (2013.01); *G06T 2207/10104* (2013.01); *G06T 2207/10108* (2013.01); *G06T 2207/10121* (2013.01); *G06T 2207/20076* (2013.01); *G06T 2207/20084* (2013.01); *G06T 2207/30021* (2013.01)

(58) Field of Classification Search
CPC . G06T 2207/10104; G06T 2207/10108; G06T 2207/20076; G06T 2207/20084; G06T 2207/10121; G06T 2207/30021; G06T 7/70; G06T 7/0012; A61B 90/37; A61B 5/064; A61B 5/7264; A61B 2090/364; A61B 2090/3966; A61B 2090/3983; A61B 5/061; A61F 2/82; A61F 2250/0098; A61M 25/104
See application file for complete search history.

(56) References Cited

U.S. PATENT DOCUMENTS

2017/0068792 A1* 3/2017 Reiner ................. A61B 5/0022
2017/0308770 A1* 10/2017 Jetley .................. G06K 9/4671
2018/0211389 A1* 7/2018 Auvray ................ A61B 6/032

FOREIGN PATENT DOCUMENTS

WO    WO-2015173821 A1 * 11/2015  ............ A61B 6/504
WO       2017016885 A1    2/2017

OTHER PUBLICATIONS

Pierre Ambrosini et al: "Fully Automatic and Real-Time Catheter Segmentation in X-Ray Fluoroscopy"; arxiv.org, Cornell University Library, 201 Olin Library Cornell University Ithaca, NY 14853, Jul. 17, 2017 (Jul. 17, 2017), XP080777275; DOI: 10.1007/978-3-319-66185-8 65.
European Search Report for corresponding Appln. No. EP18177904 dated Dec. 5, 2018.
Long et al., "Fully Convolutional Networks for Semantic Segmentation", Proceedings of the IEEE International Conference on Computer Vision and Pattern Recognition, pp. 3431-3440, 2015.
Ronneberger, O., Fischer, P., & Brox, T.: "U-net: Convolutional networks for biomedical image segmentation", Computer Science Department and BIOSS Centre for Biological Signalling Studies, University of Freiburg, pp. 234-241, 2015.
Tompson, J. et al., "Joint Training of a Convolutional Network and a Graphical Model for Human Pose Estimation" Advances in Neural Information Processing Systems, pp. 1799-1807, 2014.
Jia, Yangqing, et al. "Caffe: Convolutional architecture for fast feature embedding." Proceedings of the 22nd ACM International conference on Multimedia. ACM, 2014.
Kingma, Diederik P. et al.: "Adam: A Method for Stochastic Optimization"; ICLR Conference paper; 2015., pp. 1-15.

* cited by examiner

| Architecture | Accuracy | N-accuracy |
|---|---|---|
| Direct Detection | 0.7704 | 0.7434 |
| Architecture 300 | 0.8487 | 0.8687 |
| Architecture 400 | 0.8970 | 0.9034 |
| Architecture 500 | 0.9024 | 0.9090 |

METHOD OF DETERMINING A CORRESPONDENCE BETWEEN FRAMES OF MEDICAL IMAGE DATA WITH AND WITHOUT CONTRAST MEDIUM THROUGH PROBABILITY DISTRIBUTION MAPS RELATING TO POSITION OF A FEATURE

RELATED CASE

This application claims the benefit of U.S. Provisional Application Ser. No. 62/581,983, filed Nov. 6, 2017 and claims benefit to European Application No. EP 18177904, filed on Jun. 15, 2018, which claims benefit to the US Provisional Application above, all of which are hereby incorporated by reference in their entirety.

FIELD

The embodiments relate in one aspect to a method of determining a correspondence between frames of a set of medical image data. In further aspects, the embodiments relate to a medical imaging apparatus and a computer program product.

BACKGROUND

In certain medical procedures that involve intraoperative guidance, there is often benefit in introducing a contrast medium to a patient's body to highlight or make visible anatomical structures in an image being acquired during the procedure. For example, in certain cardiology procedures, a contrast medium may be delivered into a patient to highlight, in a fluoroscopic image, blood vessels into which a medical practitioner is inserting a medical device.

Although the delivery of such a contrast medium can increase the visibility of anatomical structures, such as blood vessels, in some circumstances the contrast medium can also act to obscure or occlude structures, such as medical devices within those anatomical structures. The medical devices would otherwise be clearly visible in an image acquired without the use of a contrast medium. In such circumstances, it can be difficult for the medical practitioner to determine the location of a feature of the medical device once the contrast medium has been delivered. This may, at least partly, negate the usefulness of image guidance for the procedure. For example, in frames acquired with contrast medium, the location of a catheter tip may be ambiguous as the tip is occluded by the contrast medium, making it difficult for a medical practitioner to identify the location of the catheter tip only with information present within those frames.

SUMMARY AND DETAILED DESCRIPTION

A method, medical imaging apparatus, and the computer program product may solve the problem of the medical device being occluded by contrast agent.

The embodiments relate in one aspect to a method of determining a correspondence between frames of a set of medical image data. The set of medical image data includes at least one frame acquired without contrast medium and at least one frame acquired with contrast medium. The method includes:

receiving first data representing a first image frame acquired without contrast medium; receiving second data representing a second image frame acquired with contrast medium; and determining a position of a feature of a medical instrument in the second image frame at least partly on the basis of a position of the feature determined from the first image frame.

One embodiment relates in one aspect to a method wherein the position of the feature in the second image frame and the position of the feature in the first image frame are each determined using a respective neural network.

One embodiment relates in one aspect to a method wherein the position of the feature in the second image frame is determined at least partly on the basis of a position of one or more anatomical features determined in both the first image frame and the second image frame.

One embodiment relates in one aspect to a method including: concatenating the first data and the second data to generate a two-channel image dataset; inputting the two-channel image dataset to the neural network; and outputting, from the neural network, a first probability distribution map relating to a position of the feature in the first image frame and a second probability distribution map relating to a position of the feature in the second image frame.

One embodiment relates in one aspect to a method including: receiving the first data at a first neural network; outputting, from the first neural network, a first probability distribution map relating to the position of the feature in the first image frame; concatenating the first probability distribution map with the first data and the second data to generate a three-channel image dataset; receiving the three-channel image dataset at a second neural network; and outputting, from the second neural network, a second probability distribution map relating to the position of the feature in the second image frame.

One embodiment relates in one aspect to a method including: concatenating the first probability distribution map with the second probability distribution map to generate a third, two-channel, probability distribution map; applying an activation function to the two-channel probability distribution map to generate a fourth, single-channel probability distribution map relating to regions of interest for detecting the feature in the first and second image frames; and performing an elementwise multiplication of the fourth probability distribution map and the second probability distribution map to generate a fifth probability distribution map relating to the position of the feature in the second image frame.

One embodiment relates in one aspect to a method wherein the activation function is a sigmoid function.

One embodiment relates in one aspect to a method wherein the first image frame is a frame corresponding to an earliest time period in the set of image data.

One embodiment relates in one aspect to a method wherein the set of medical image data represents a medical image of a patient.

One embodiment relates in one aspect to a medical device including one or more of: a tip of a catheter; a marker attached to an angioplasty balloon; and a marker attached to a coronary stent.

The embodiments relate in one aspect to a medical imaging apparatus for determining a correspondence between frames of a set of medical image data. The set of medical image data include at least one frame acquired without contrast medium and at least one frame acquired with contrast medium. A processor is configured to: receive first data representing a first image frame acquired without contrast medium; receive second data representing a second image frame acquired with contrast medium; and determine a position of a feature of a medical device in the second image frame at least partly on the basis of a position of the feature determined from the first image frame.

One embodiment relates in one aspect to a medical imaging apparatus wherein the processor is configured to: receive the first data at a first neural network; output, from the first neural network, a first probability distribution map relating to the position of the feature in the first image frame; concatenate the first probability map with the first data and the second data to generate a three-channel image dataset; input the three-channel image dataset to a second neural network; and output, from the second neural network, a second probability distribution map relating to the position of the feature in the second image frame.

One embodiment in one aspect relates to a medical imaging apparatus wherein the processor is configured to: concatenate the first probability distribution map with the second probability distribution map to generate a third, two-channel, probability distribution map; apply an activation function to the two-channel probability distribution map to generate a fourth, single-channel, probability distribution map relating to regions of interest for detecting the feature in the first and second image frames; and perform an elementwise multiplication of the fourth probability distribution map and the second probability distribution map to generate a fifth probability distribution map relating to the position of the feature in the second image frame.

One embodiment relates in one aspect to a medical imaging apparatus including a display unit configured to display a video image representing the frames of the set of medical image data. The processor is configured to: generate an overlay representing the position of the feature in the second image frame based on one or more of the first, second and fifth probability distribution maps; apply the overlay to the second image frame to generate an annotated image frame; and display the annotated image frame on the display unit.

One embodiment relates in one aspect to a medical imaging apparatus wherein the processor is configured to detect a delivery of contrast medium and to determine that the second image frame is a frame acquired with contrast medium on the basis of the detection.

The embodiments relate in one aspect to a computer program (instructions executable by a processor) stored on a non-transitory computer readable storage medium, the computer program being loadable into a memory unit of a data processing system and including program code sections to make a data processing system execute the method when the computer program is executed in said data processing system.

The computer program product can be, for example, a computer program or be another element apart from the computer program. This other element can be hardware, for example a memory device, on which the computer program is stored, a hardware key for using the computer program and the like, and/or software, for example a documentation or a software key for using the computer program.

The medical imaging apparatus can, for example, be selected from the group of an X-ray fluoroscopy device, a computed tomography device, a magnetic resonance imaging device, a molecular imaging device, a single photon emission computed tomography (SPECT) device, a positron emission tomography (PET) device and combinations thereof. The medical imaging device can be, for example, a combination of an imaging modality and a therapy modality, in particular a radiation therapy modality.

Reference is made to the fact that the described methods and the described imaging apparatus are merely preferred example embodiments of the invention and that the invention can be varied by a person skilled in the art, without departing from the scope of the invention provided it is specified by the claims. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION

Figure 1:
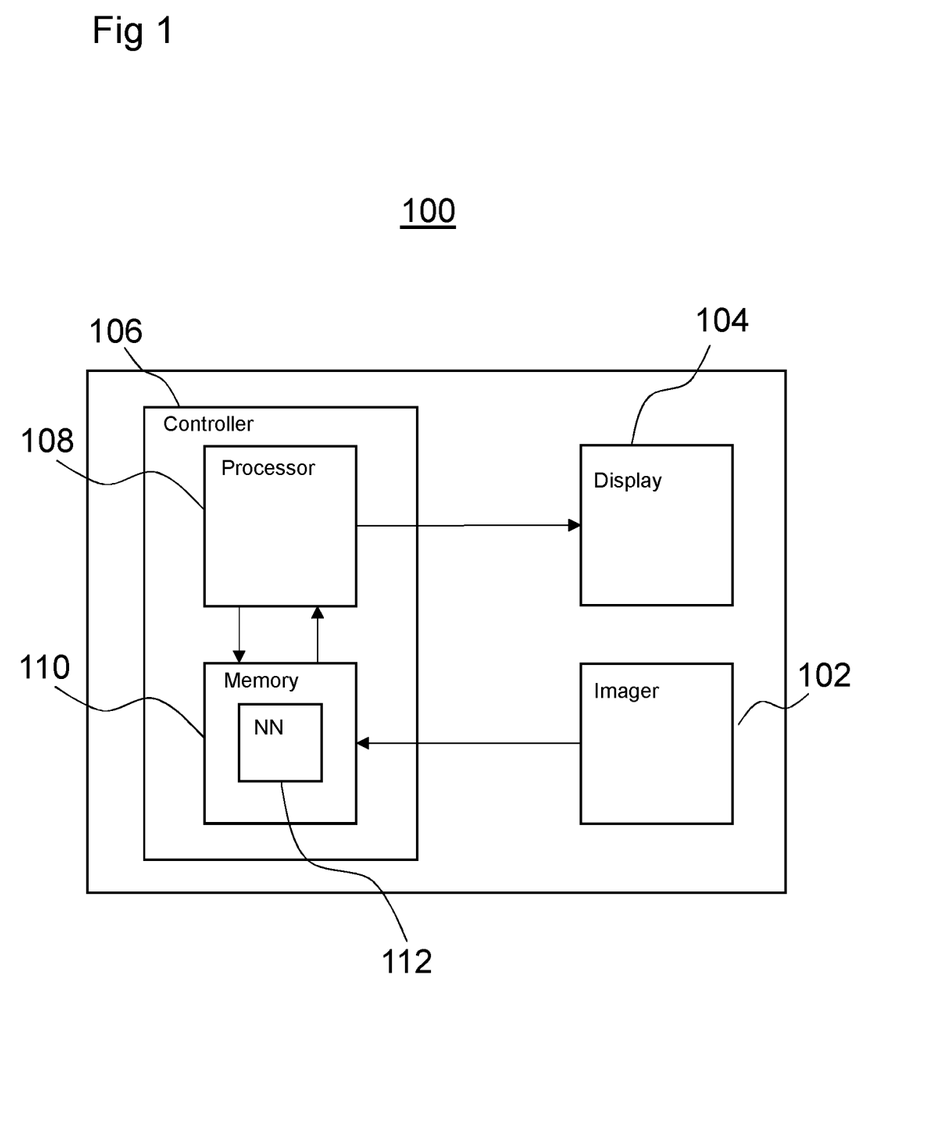
FIG. 1 is a schematic diagram of a medical imaging apparatus according to one embodiment.

FIG. 1 is a diagram illustrating a medical imaging apparatus 100 according to an embodiment. The medical imaging apparatus 100 includes an imager or imaging unit 102 arranged to generate image data according to a particular imaging modality. For example, the imager 102 may be an X-ray fluoroscopy system arranged to generate X-ray fluoroscopy images and present them on a display 104.

The medical imaging apparatus 100 may include a controller 106 for controlling one or more parameters of the medical imaging apparatus 100. For example, the controller 106 may control images presented on the display 104 and may be arranged to generate display data, based on image data generated by the imaging unit 102, for controlling display parameters of the display 104.

The controller 106 may be implemented using hardware and/or software. In some examples, the controller 106 may include a processor 108 and a memory 110.

The memory 110 may be configured to store data in the form of one or more neural networks 112 that are trained by implementing a machine learning algorithm prior to installation and use of the medical imaging apparatus 100 in an operation setting. For example, the neural networks 112 may be trained by supplying training data to the neural networks 112, as described below, and the machine learning algorithm may learn to determine a correspondence between frames of a set of medical image data. The processor 108 may be arranged to preform functions as described herein, in conjunction with the memory 110, for example.

The machine learning algorithm may be any suitable algorithm implementing an artificial neural network for determining a correspondence between frames of a set of medical image data. For example, the machine learning algorithm may be a convolutional neural network (CNN) algorithm or a fully convolutional neural network (FCN) algorithm, such as an algorithm implemented by an architecture that enables the one or more neural networks 112 to be trained to determine transformations between coordinate frames of sets of image data. In another example, the machine learning algorithm may be a multilayer perceptron (MLP) algorithm.

Furthermore, the memory 110 may store a computer program executable by the processor 108, to perform the methods described herein, and specifically the method described below with reference to FIG. 2.

The memory 110 may be any suitable form of memory. For example, the memory 110 may comprise volatile memory, such as random access memory (RAM), and/or non-volatile memory, such as read only memory (ROM) or flash memory. Furthermore, the memory 110 might comprise multiple, separate, memory devices and may comprise a combination of volatile and non-volatile memory. In some examples, certain components, such as the computer program, may be stored in one memory device, while other components may be stored in another memory device.

Figure 2:
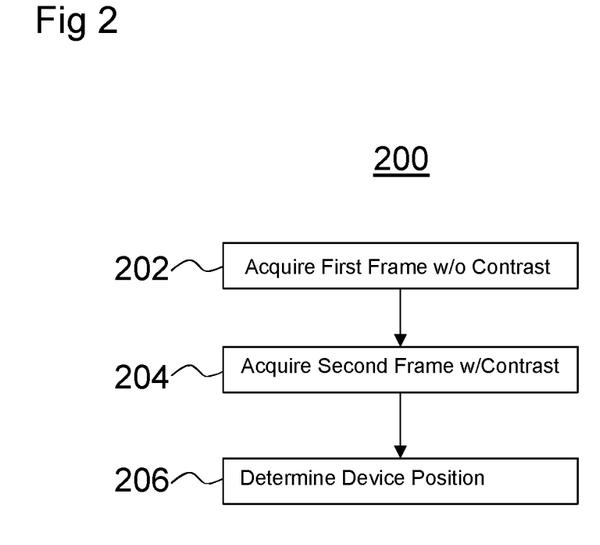
FIG. 2 is a simplified workflow diagram illustrating a method according to one embodiment.

FIG. 2 is a flow diagram depicting a method 200 of determining a correspondence between frames of a set of medical image data. The method 200 may, for example, be implemented by software or firmware executed by the controller 106 described above with reference to FIG. 1.

At block 202, first data representing a first image frame acquired without contrast medium is received. For example, the first data may be received by the processor 108 of the controller 106 described above with reference to FIG. 1.

The first data may, for example, be data representing a frame corresponding to an earliest period in the set of image data. In particular, within a set of image data there may be frames acquired with contrast medium and frames that are acquired without contrast medium. However, given that a medical practitioner typically delivers contrast medium during a medical procedure (for example, by injecting the contrast medium), it may be assumed that at least the first frame of the set of image data is acquired without contrast medium.

At block 204, second data representing a second image frame acquired with contrast medium is received. For example, the first data may be received by the processor 108 of the controller 106 described above with reference to FIG. 1.

The second image data may, for example, be data representing a frame corresponding to a time subsequent to the earliest time period (i.e. subsequent to the time period to which the first data corresponds). In some embodiments, the processor 108 of the controller 106 may be arranged to detect delivery of contrast medium and to determine that the second image frame is a frame acquired with contrast medium on the basis of the detection of the delivery of contrast medium. For example, it may be determined that the second image frame is a frame acquired with contrast if it corresponds to a time period subsequent to the delivery of contrast medium.

At block 206, a position of a feature of a medical device in the second image frame is determined at least partly on the basis of a position of the feature determined from the first image frame. For example, the position of the feature in the second image frame and the position of the feature in the first image frame are each determined using a respective neural network, such as the neural networks 112 described above with reference to FIG. 1.

The position of the feature in the second image frame may be determined at least partly on the basis of a position of one or more anatomical features determined in both the first image frame and the second image frame. That is, anatomical structures that are imaged in both the first and second image frames may provide contextual information that is not significantly affected by the presence of contrast medium, which may aid in determining the position of the feature in the second image frame.

Typically, the shape and location of the feature of the medical device does not change significantly with respect to anatomical structures forming the background of an image formed by each frame between frames of the image data set (i.e. within a time frame corresponding with a time frame over which a medical procedure is carried out and which the image data set covers). Without a contrast medium, teaching a neural network to identify the location of a solid medical device may be straightforward as such devices typically provide a high contrast with respect to the soft tissue of a patient into which the device has been inserted. However, the learning task becomes more difficult when it involves delivery of a contrast medium because, as described above, the contrast medium obscures or occludes the medical device in images acquired in the presence of the contrast medium. Thus, in the present embodiment, frames acquired where there is no contrast medium present and in which a position or location of a feature of the medical device can been determined are used to aid determination of the position or location of the same feature of the medical device, in the same image data set, in frames in which contrast medium is present. This may enable a more precise location or position of the feature in frames acquired with contrast medium, because the detection result provided by analysing the frame acquired without contrast medium provides an inference of the shape and location of the feature, which can be used to assist the determination of the position or location of the feature in an image frame acquired in the presence of contrast medium.

The feature of the medical device may be one or more of: a tip of a catheter; a marker attached to an angioplasty balloon; and a marker attached to a coronary stent. In other implementations, the feature may be any feature of a medical device recognisable by the neural networks 112.

Using the method 200 described with reference to FIG. 2 is advantageous over treating the problem of obscured or occluded medical devices as a tracking problem and receiving the whole set of image data (i.e. a complete video) into a neural network in a recurrent fashion.

It is not always necessary for the position of the feature of the medical device to be identified to a medical practitioner in every single frame of the image data set. In practice, it may be sufficient to only determine the position of the feature of the medical device in a frame (or frames) selected by the medical practitioner (i.e. those frames that relevant for carrying out the medical procedure). For example, it may be sufficient for the medical practitioner to be able to identify the blood vessel branch in which a catheter tip is located in certain image frames selected by the medical practitioner. Furthermore, once the neural network has been trained, the computation time for determining the position of a feature of the medical device in a given image frame is significantly lower that the time that would be required to determine the location of the feature of the medical device in every frame of the set of image data. Analysing the complete set of image data would be computationally intensive and would accordingly affect the performance of the medical imaging apparatus.

Figure 3:
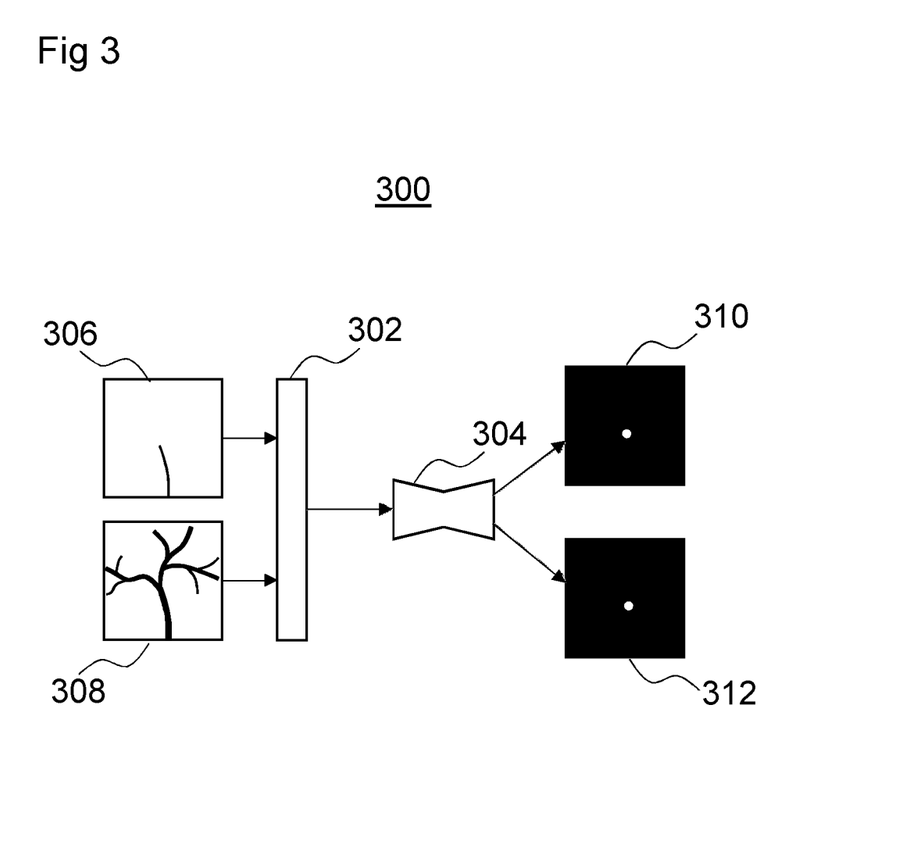
FIG. 3 is a schematic diagram of an architecture for determining a correspondence between frames of a set of medical image data according to one embodiment.

FIG. 3 is a schematic diagram of an architecture 300 for determining a correspondence between frames of a set of medical image data according to one embodiment. For example, the architecture 300 shown in FIG. 3 may be an implementation of the neural networks 112 described above with reference to FIG. 1.

The architecture 300 shown in FIG. 3 includes a concatenation operator 302 and a neural network 304.

The concatenation operator 302 is configured to concatenate first data, representing a first image frame 306 acquired without contrast medium, and second data, representing a second image frame 308 acquired with contrast medium. The concatenation operator 302 is configured to generate a two-channel image dataset, in which one channel is the first data and the other channel is the second data.

The neural network 304 is configured to receive the two-channel image dataset and to output two probability distribution maps: a first probability distribution map 310 relating to a position of the feature in the first image frame 306 and a second probability distribution map 312 relating to a position of the feature in the second image frame 308. The neural network 304 may be a U-net with convolution, ReLU layers with down sampling to convolution ReLu layers with drop out before a bridge, in the bridge, and after the bridge (the bridge being at a level of greatest abstraction between encoder and decoder), and up sampling to convolution ReLU layers. Any number of layers and any number of convolution blocks at each layer (i.e., each level of abstraction) may be used. Feedfoward or skip connections may be provided, such as connecting layers in the encoder with layers of the decoder at the same level of abstraction or resolution.

In some embodiments, the first probability distribution map 310 may be used to validate that the neural network 304 is able to determine the position of the feature in the first image frame 306; for example, the position of the feature in the first image frame 306 determined by the neural network 304 may be compared with ground truth data and the position of the feature in the first image frame 306 determined by the neural network may be deemed to be correct if a difference between the determined position and the ground truth position is equal to or lower than a threshold value. If the difference is greater than the threshold value, the controller 106 may determine that a position of the feature in the second image frame 308 (i.e. an image frame acquired with contrast medium), determined by neural network 308, is unreliable.

The probability distribution maps 310, 312 (sometimes referred to as heat maps) each represent a distribution of the probability that the feature is located at positions within the respective distribution maps 310, 312. In other words, the probability distribution maps 310, 312 relate to the likely position of the feature of the medical device in the respective image frame 306, 308. For example, a location in the probability distribution map that has a highest probability value may be determined to correspond to the position of the feature of the medical device in the respective image frame 306, 308.

Providing the neural network 304 with information regarding the probable location of the feature in the first image frame 306 acquired without contrast medium (i.e. information corresponding to the first probability distribution map 310), affects the second probability distribution map 312 generated by the neural network 304. That is, the probable position of the feature of the medical device in the first image frame 306 affects the determined probable position of the feature of the medical device in the second image frame 308, because the result of the determination of the position of the feature of the medical device in the first image frame 306 may provide an approximate position of the feature of the medical device in the second image frame 308. With the additional information provided by determining the position of the feature of the medical device in the first image frame, it is easier for the neural network 304 to determine a position or location of the feature of the medical device in the second image frame 308. Furthermore, the neural network 304, appropriately trained using training data, is able to make a more accurate determination of the location of the feature in the second image frame 308 and other image frames acquired with contrast medium, as compared to a direct determination of the position of the feature in the second image frame 308 (i.e. without the information determined from the first image frame 306).

Figure 4:
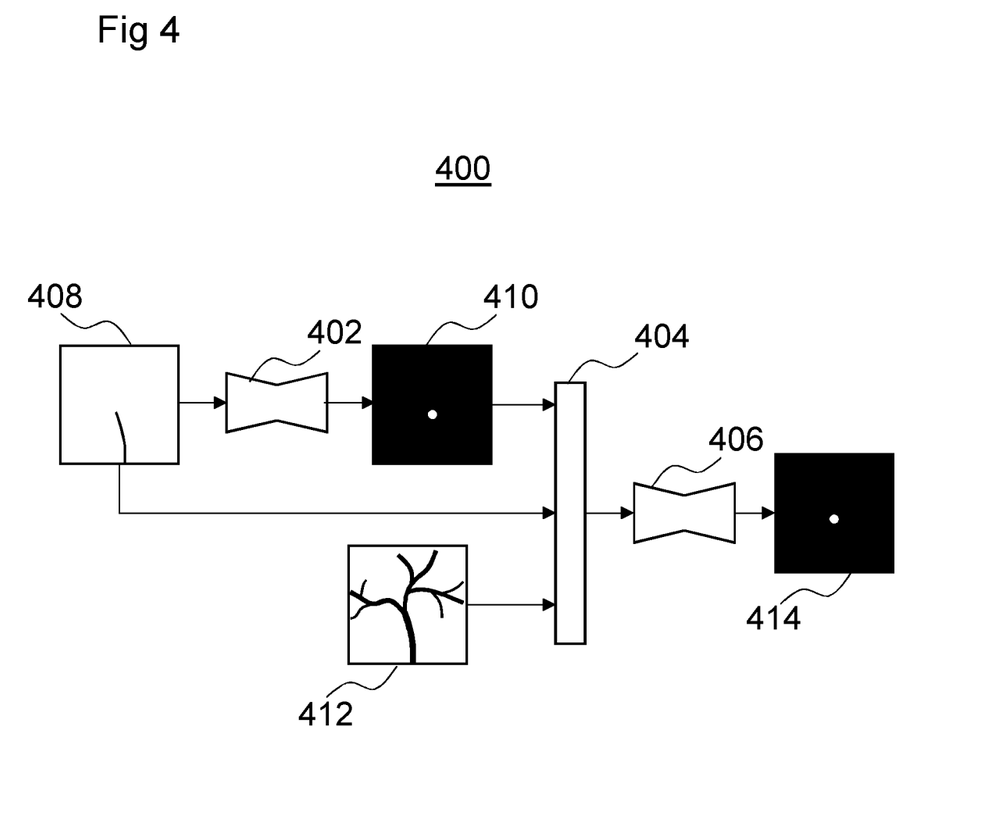
FIG. 4 is a schematic diagram of an architecture for determining a correspondence between frames of a set of medical image data according to one embodiment.

FIG. 4 is a schematic diagram of an architecture 400 for determining a correspondence between frames of a set of medical image data according to another embodiment, which may be an implementation of the neural networks 112 described above with reference to FIG. 1.

The architecture 400 shown in FIG. 4 includes a first neural network 402, a concatenation operator 404, and a second neural network 406.

The first neural network 402 is arranged to receive first data (representing a first image frame 408 acquired without contrast medium and to output a first probability distribution map 410 relating to the position of the feature of the medical device in the first image frame 408.

The concatenation operator 404 is arranged to receive and concatenate the first data (representing the first image frame 408), the first probability distribution map 410 output by the first neural network 402, and second data (representing a second image frame 412 acquired with contrast medium) to generate a three-channel image dataset. The three-channel image dataset has one channel of the first data, one channel of the first probability distribution map 410 and one channel of the second data.

The second neural network 406 is arranged to receive the three-channel image dataset output from the concatenation operator 404, and to output a second probability distribution map 414 relating to the position of the feature in the second image frame 412.

The architecture 400 can be thought of as implementing a two-stage process. In the first stage, an image frame (such as the first image frame 408) that is acquired without contrast medium is fed into a neural network (i.e. the first neural network 402) to generate or produce a probability distribution map (sometimes referred to as a heat map), from which a likely location or position of the feature of the medical device in that image frame can be inferred. The purpose of the first stage is to determine a likely position of the feature in the image frame acquired without contrast medium. In the second stage, the image frame acquired with a contrast medium, an image frame acquired without contrast medium, and the probability distribution map 410 generated based on the image frame acquired without contrast medium, are concatenated as inputs into another neural network (i.e. the second neural network 406). The purpose of the second stage is to determine a likely position or location of the feature in the image frame acquired with contrast medium (i.e. the second image frame 412).

In this two-stage process, which may be referred to as sequential detection, the first stage of determining a location or position of the feature of the medical device in the image frame acquired without the presence of a contrast medium is an intermediate step that provides information that can be leveraged in the second stage to provide a more accurate determination of the location or position of the feature of the medical device in the image frame acquired in the presence of a contrast medium.

In other words, the result of the first stage may be utilized to assist in the second stage by providing a rough location or position of the feature of the medical device. With this assistance, it is easier for the second neural network 406 to determine a position or location of the feature of the medical device in the image acquired in the presence of a contrast medium. As a result, by leveraging information regarding the location of the feature of the medical device in the frame acquired without contrast medium (determined by the first neural network 402), the second neural network 406, appropriately trained using training data, is able to make a more precise determination of the location of the feature in frames acquired with contrast medium.

The first and second neural networks 402, 406 that perform the two stages may share or be part of a common architecture, but weightings applied to the components of the neural networks 402, 406 may differ, as dictated by a training process. Two U-nets may be used for the networks 402, 406.

Figure 5:
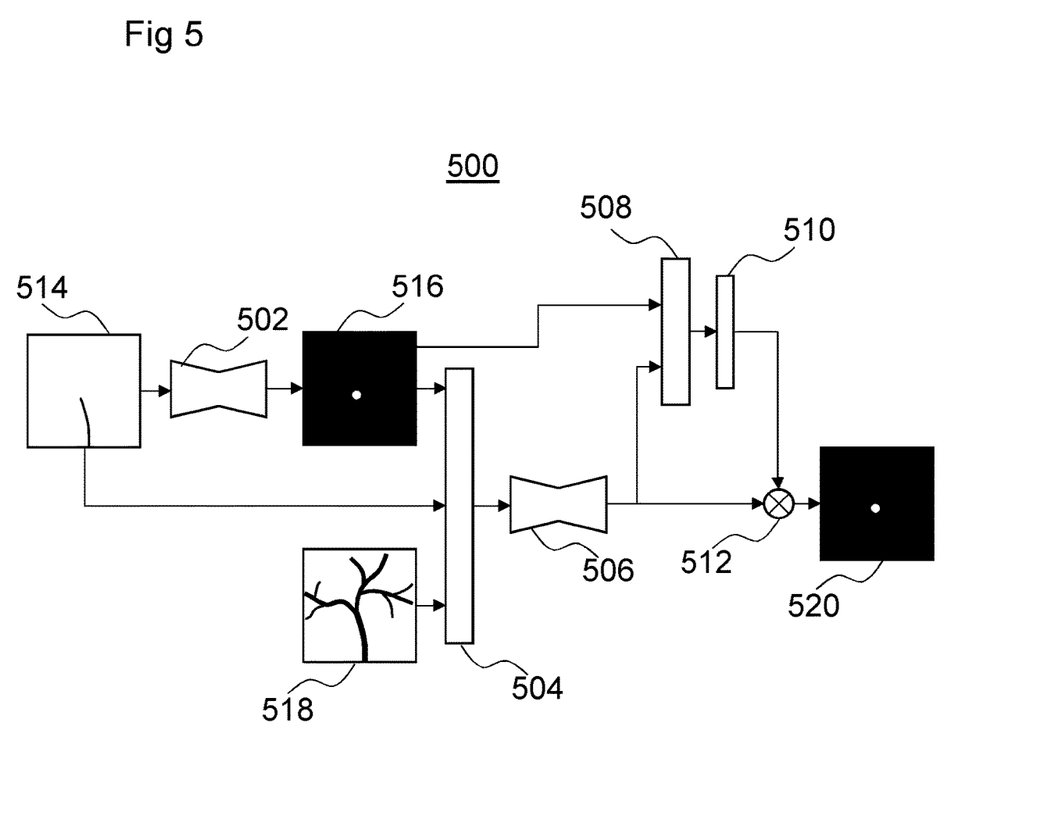
FIG. 5 is a schematic diagram of an architecture for determining a correspondence between frames of a set of medical image data according to one embodiment.

FIG. 5 is a schematic diagram of an architecture 500 for determining a correspondence between frames of a set of medical image data according to another embodiment, which may be an implementation of the neural networks 112 described above with reference to FIG. 1.

Similar to the architecture 400 described above with reference to FIG. 4, the architecture 500 shown in FIG. 5 includes a first neural network 502, a first concatenation operator 504, and a second neural network 506. The first and second neural networks 502, 506 may share a common architecture, but weightings applied to the components of the neural networks may differ, as required and dictated by a training process. Two U-nets may be used for the networks 502, 506.

The architecture 500 shown in FIG. 5 also include a second concatenation operator 508, an activation function operator 510, and an elementwise multiplication function operator 512.

Similar to the first neural network 402 described above with reference to FIG. 4, the first neural network 502 is arranged to receive first data (representing a first image frame 514 acquired without contrast medium) and to output a first probability distribution map 516 relating to the position of the feature of the medical device in the first image frame 514.

The first concatenation operator 504 is arranged to receive and concatenate the first data (representing the first image frame 514), the first probability distribution map 516 output by the first neural network 502, and second data (representing a second image frame 518 acquired with contrast medium) to generate a three-channel image dataset. The three-channel image dataset has one channel as the first data, one channel as the first probability distribution map 516 and one channel as the second data.

The second neural network 506 is arranged to receive the three-channel image dataset output from the concatenation operator 504, and to output a second probability distribution map.

Similar to the architecture 400 described above with reference to FIG. 4, the architecture 500 shown in FIG. 5 implements a two-stage process (i.e. sequential detection) in which the result of the first stage may be utilized to assist in the second stage (i.e. in respect of determining a feature in the second image frame 518, acquired with contrast medium) by providing a rough location or position of the feature. However, in the architecture 500 shown in FIG. 5, rather than second neural network 506 outputting a probability distribution map relating to the position of the feature in the second image frame 512 (as is done by the second neural network 406 described above with reference to FIG. 4), the second probability distribution map output by the second neural network 506 shown in FIG. 5 is subjected to further processing.

In particular, the architecture 500 is capable of not only learning to determine a position of a feature of a medical device in frames acquired with and without contrast medium, but it is also capable of learning a relationship between image frames acquired with contrast medium and image frames acquired without contrast medium. The mechanism for determining the relationship between image frames acquired with contrast medium and image frames acquired without contrast medium is referred to herein as an "attention" mechanism, by which the architecture 500 can take account of contextual information relating to features of the respective image frames (i.e. those acquired with and without contrast medium). As described above, such contextual information may be provided by, for example, background anatomical features that do not change significantly following delivery of the contrast medium. Using this attention mechanism provides improved determination of a position of a feature of a medical device with respect to the architecture 400 described above with reference to FIG. 4.

In order to provide the attention mechanism, the second concatenation operator 508 is arranged to concatenate the second probability distribution map with the first probability distribution map 516, to generate a third, two-channel, probability distribution map. The activation function operator 510 is arranged to apply an activation function to the third (two-channel) probability distribution map output from the second concatenation operator 508 to generate a fourth, single-channel, probability distribution map. The fourth probability distribution map relates to regions of interest for detecting the feature in the first and second image frames 514, 518. For example, the activation function applied by the activation function operator 508 may be a sigmoid function.

The elementwise multiplication function operator 512 is arranged to perform an elementwise multiplication of the fourth probability distribution map and the second probability distribution map to generate a fifth probability distribution map 520 relating to the position of the feature of the medical device in the second image frame 518. In particular, each element of the fourth probability distribution map (which corresponds to a two-dimensional matrix of elements) is multiplied with the corresponding element of the second probability map (which also corresponds to a two-dimensional matrix of elements) such that the each of the elements of the resulting fifth probability distribution map 520 is a product of the respective elements of the fourth and second probability maps.

By concatenating the outputs of the first neural network 502 with the output from the second neural network 506, and applying the activation function operator 510 and the elementwise multiplication function operator 512 to the output of the second concatenation operator 508, the architecture 500 shown in FIG. 5 is capable of performing the attention mechanism, thereby learning a relationship between image frames acquired with contrast medium (e.g. the first image frame 514) and frames acquired without contrast medium (e.g. the second image frame 18).

The attention mechanism may be described as follows. Denoting the outputs of the first and second neural networks 502, 506 (i.e. the first probability distribution map 516 and the second probability distribution map) as $f_1$ and $f_2$, and the output of the second concatenation operator 508 (i.e. the third probability distribution map, which is a concatenation of $f_1$ and $f_2$) as f, the output of the activation function operator 510 (i.e. the fourth probability distribution map, which may be referred to as an attention map) $g \in \mathbb{R}^{H \times W}$ (i.e. g belongs to a real matrix of size H×W) is computed as follows:

$$g = \sigma(\alpha * f + b)$$

where σ is a sigmoid function, * is a convolution, and α and b denote convolution kernels and bias respectively. Then g is applied by the elementwise multiplication function operator 512 to define a refinement $f_2^{att}$ of $f_2$ using the fourth probability distribution map, g:

$$f_2^{att} = f_2 \circ g$$

where ○ denotes a Hadamard product operation, in which elements of matrices representing the second and fourth probability distribution maps are multiplied on an elementwise basis as described above (i.e. $f_2^{att}(i,j) = f_2(i,j) \times g(i,j)$, where i and j are rows and columns of matrices corresponding to the respective probability distribution maps). The refined feature $f_2^{att}$ is used to compute the fifth probability distribution map 520 relating to the position of the feature of the medical device in the second image frame 518.

Using this attention mechanism, predictions of position or location of the feature of the medical device in the second image frame 518 (acquired with contrast medium) is influenced or regulated by the attention map (i.e. the fourth probability distribution map), which indicates a region of interest of the first and second image frames 514, 518, in which the neural networks 502, 506 of the architecture 500 should focus for detecting the feature of the medical device. In other words, summarizing together information regarding the likely position of the feature of the medical device in the frame acquired without contrast medium with information regarding the likely position of the feature of the medical device in the frame acquired with contrast medium enables the architecture 500 to determine a region of interest by providing prior knowledge regarding an approximate location of the feature of the medical device.

To train the neural networks described above with reference to FIGS. 3 to 5, each set of image data may be separated (for example, manually by a technician) into image frames acquired with contrast medium and image frames acquired without contrast medium. During training, image frames acquired with contrast medium may be paired with image frames, from the same image set, that are acquired without contrast medium. These pairs may be fed into a neural network architecture, such as those described above with reference to FIGS. 3 to 5, to detect features of the medical device in the respective image frames.

With reference to the architectures 400, 500 described with reference to FIGS. 4 and 5, the neural networks 402, 406, 502, 506 that form the two stages are trained in an end-to-end fashion such that the architectures 400, 500 may learn to detect not only locations of the feature of the medical device in the image frames acquired with and without contrast medium but may also learn the relation between image frames acquired with and without contrast medium.

Once the neural networks have been trained, the resulting trained networks may be tested. During testing, the neural networks are not provided with information regarding whether a given image frame is one that was acquired with contrast medium, or one that was acquired without contrast medium. Nevertheless, as explained above, the controller 106 may assume that the first image frame in a given image data set is one acquired without contrast medium. Accordingly, each image frame subsequent to the first image frame in an image data set, that is determined to be acquired with contrast medium, may be paired with the first image frame in the image data set.

Figure 6:
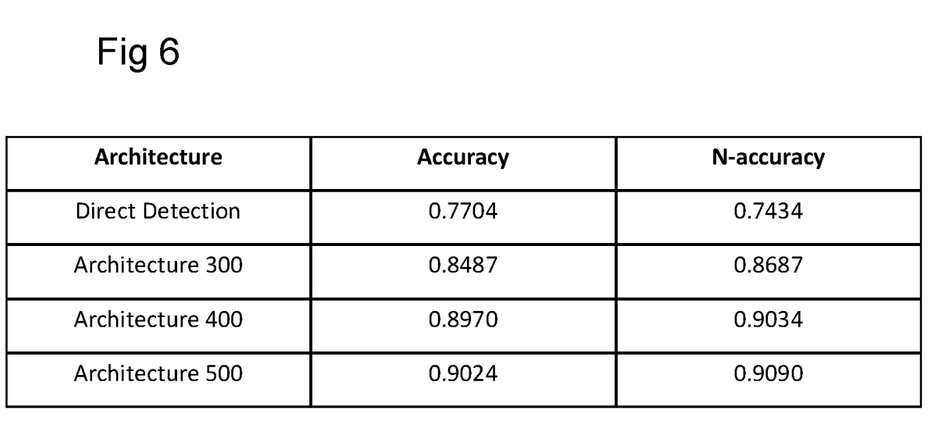
FIG. 6 is a table showing the relative accuracies of architectures for determining a correspondence between frames of a set of medical image data according to one embodiment.

FIG. 6 shows the results of testing the architectures 300, 400, 500 described above with reference to FIGS. 3 to 5 compared with an architecture arranged to directly determine the position of a feature of a medical device in an image frame acquired with contrast medium (referred to as direct detection). Each of the architectures is compared with ground truth data and, if a Euclidean distance between the position determined using the respective architecture and the ground truth position is less than a threshold value, the determination by the respective architecture is considered to be a positive determination.

An accuracy value is determined as the ratio of positive determinations compared to the number of image frames acquired with contrast medium.

$$accuracy = \frac{\text{number of positive determinations}}{\text{number of image frames with contrast medium}}$$

As the size of the sets of image data is variable (i.e. the length of videos is variable), a normalized accuracy (N-accuracy) is defined to remove any bias introduced by the variable size. The normalized accuracy is defined as:

$$N - accuracy = \frac{\sum_{i=1}^{N} accuracy_i}{N}$$

The comparisons shown in FIG. 6 indicate that each of the architectures 300, 400 500 exhibit higher accuracy and normalized accuracy that direct detection. Furthermore, FIG. 6 shows that the architecture 400 described with reference to FIG. 4 exhibits higher accuracy and normalized accuracy than the architecture 300 described with reference to FIG. 3, and that the architecture 500 described with reference to FIG. 5 exhibits higher accuracy and normalized accuracy than the architecture 400 described with reference to FIG. 4.

Figure 7A:
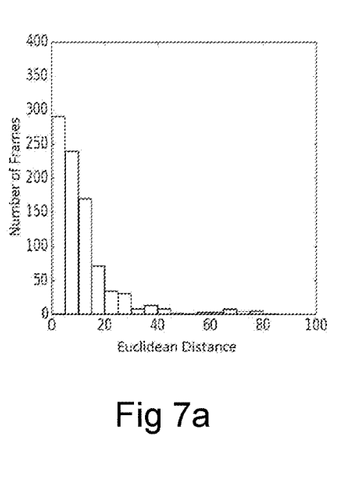
FIG. 7a is a histogram of the number of image frames versus Euclidean distance between a position determined using direct detection and a ground truth position.
Figure 7B:
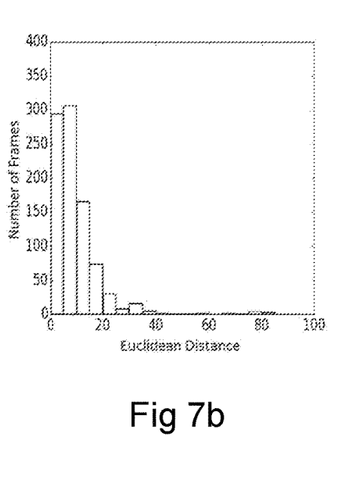
FIG. 7b is a histogram of the number of image frames versus Euclidean distance between a position determined using the architecture of FIG. 3 and a ground truth position.
Figure 7C:
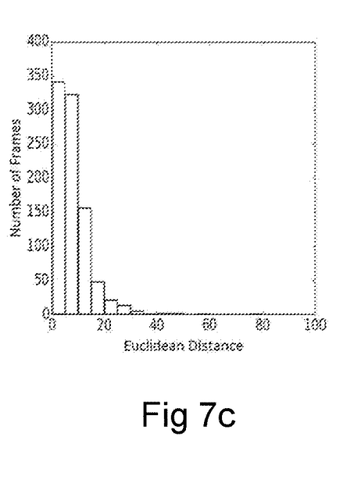
FIG. 7c is a histogram of the number of image frames versus Euclidean distance between a position determined using the architecture of FIG. 4 and a ground truth position.
Figure 7D:
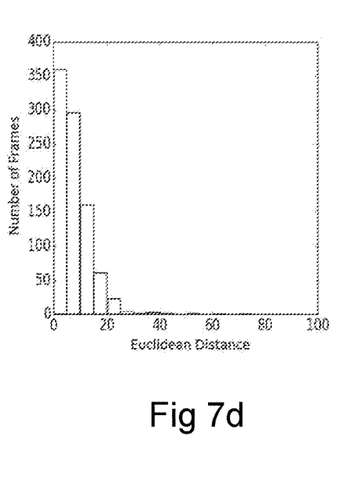
FIG. 7d is a histogram of the number of image frames versus Euclidean distance between a position determined using the architecture of FIG. 5 and a ground truth position.

FIGS. 7a to 7d show histograms of the number of image frames versus Euclidean distance between the position determined using the respective architecture and the ground truth position for direct detection (FIG. 7a), the architecture 300 described with reference to FIG. 3 (FIG. 7b), the architecture 400 described with reference to FIG. 4 (FIG. 7c), and the architecture 500 described with reference to FIG. 5 (FIG. 7d). From the histograms shown in FIGS. 7a to 7d, each of the architectures 300, 400 500 exhibit higher accuracy than direct detection, the architecture 400 described with reference to FIG. 4 exhibits higher accuracy than the architecture 300 described with reference to FIG. 3, and that the architecture 500 described with reference to FIG. 5 exhibits higher accuracy than the architecture 400 described with reference to FIG. 4.

The results of the evaluations shown in FIG. 6 and FIGS. 7a to 7d show that image frames that are acquired without a contrast medium can provide information useful for determining a position of a feature in image frames acquired with contrast medium.

This shows that prior knowledge of a position of a feature in an image frame acquired without contrast medium is beneficial to the task of determining a position of that feature in an image frame acquired with contrast medium, consistent with the shape and location of the feature of the medical device not moving significantly relative to background features between frames of a set of image data.

Furthermore, as indicated by a comparison with the architecture 400 of FIG. 4, the architecture 500 described with reference to FIG. 5, in which there is the attention mechanism described above, does not merely perform as two individual detectors, one for images frames acquired without contrast medium and one for image frames acquired with contrast medium, but additionally utilizes knowledge of the relationship between images frames acquired without contrast medium and image frames acquired with contrast medium.

In some examples, the neural networks of the respective architectures 300, 400, 500 may be provided with ground truth data representing a position of the features of the medical device in a so-called supervised learning process. Such supervised learning may increase the efficiency of the training process. For example, the ground truth data may include two-dimensional Gaussian maps whose peaks are located at the ground truth locations, and the peaks of those Gaussian maps may correspond to a target of the respective architecture 300, 400 500. The peak and standard variance of the two-dimensional Gaussian maps may be, for example, set as 10000 and 12 respectively.

In some examples relating to the architectures 400, 500 described with reference to FIGS. 4 and 5, there may be an intermediate supervision step at the end of the first stage (i.e. in relation to determination of the position of the feature of the medical device in the image frame acquired without contrast medium).

At each stage, the training process may include determination of a so-called "loss", which represents a difference between a position of the feature of the medical device as determined by the respective neural network and the ground truth position of the feature of the medical device. For example, the loss function for each stage may be calculated as mean square error. In some examples, a final loss may be computed as the summation of the loss from both stages.

The architectures 300, 400, 500 described above with reference to FIGS. 3, 4 and 5 may, for example, be implemented using a Caffe deep learning framework. During training, an initial learning rate, which defines the size of steps that the learning algorithm takes when adjusting weightings applied to the components of the neural networks during the learning process, may be set. Setting the initial learning rate appropriately provides a balance between efficient use of resources and the ability of the learning algorithm to generate optimal weightings. For example, if the learning rate is set too high, the size of the steps may be too large such that optimal values of weightings are missed (i.e. it may not be possible to achieve convergence). Conversely, if the learning rate is set too low, the learning process may be unnecessarily slow, and/or the learning process may become stuck in non-optimal minima. In some embodiments, the initial learning rate may be adjusted during the learning process to improve the balance between efficient use of resources and the ability of the learning algorithm to generate optimal weightings. For example, using a Caffe deep learning framework, the learning policy may be to set the initial learning rate to $5^{-4}$ and to decrease the learning rate using a polynomial with power of 0.9. In other embodiments, the learning rate may be fixed, or the learning rate may be decreased by a factor different to a polynomial, such as a step decrease in the rate. In other embodiments, the learning rate may be increased during the learning process.

An optimizer may be used to update parameters (i.e. weights) of the architectures 300, 400, 500 during the learning process by computing an error (determined, for example, with respect a target value) and backpropagating the error through the neural network. In some embodiments, the error may be backpropagated through the network in batches, with a batch size defining the number of data samples used to update the weightings of the network in each step. The architectures 300, 400, 500 may, for example, be optimized using an adaptive moment estimation (Adam) optimizer with a batch size of 1 that converges after being trained for around 200,000 iterations.

During testing, post-processing may be performed on the output probability distribution maps. For example, one or more of the probability distribution maps may be passed through a Gaussian filter in order to improve determination of the location of the feature of the medical device in the respective image frame. Performing such filtering may improve the robustness of the determination of the position of the feature to local maximums in the probability distribution maps.

While the invention has been illustrated and described in detail with the help of a preferred embodiment, the invention is not limited to the disclosed examples. Other variations can be deducted by those skilled in the art without leaving the scope of protection of the claimed invention.

What is claimed is:

1. A method of determining a correspondence between frames of a set of medical image data, the set of medical image data comprising at least one frame acquired without contrast medium and at least one frame acquired with contrast medium, the method comprising:
receiving, by a processor, first data representing a first image frame acquired without contrast medium, wherein the first image frame is generated by an imaging apparatus configured to capture a feature of a medical device in the first image frame;
receiving, by the processor, second data representing a second image frame acquired with contrast medium, wherein the second image frame is generated by the imaging apparatus configured to capture the feature of the medical device in the second image frame;
determining, by the processor, a position of the feature of the medical device in the second image frame, acquired with the contrast medium, at least partly on the basis of a position of the feature of the medical device determined from the first image frame acquired without contrast medium, wherein the determining further comprises:
concatenating the first data and the second data to generate a two-channel image dataset;
inputting the two-channel image dataset to at least one neural network trained to determine a correspondence between the first image frame acquired without the contrast medium and the second image frame acquired with the contrast medium by pairing the first image frame acquired without the contrast medium and the second image frame acquired with the contrast medium; and
outputting, from the at least one neural network, a first probability distribution map relating to a position of the feature in the first image frame acquired without the contrast medium and a second probability distribution map relating to a position of the feature in the second image frame acquired with the contrast medium.

2. The method according to claim 1, wherein the at least one neural network comprises a first neural network and a second neural network, and wherein the position of the feature acquired with the contrast medium in the second image frame is determined using the second neural network and the position of the feature in the first image frame acquired without the contrast medium is determined using the first neural network.

3. The method according to claim 1, wherein the position of the feature in the second image frame is determined at least partly on the basis of a position of one or more anatomical features determined in both the first image frame and the second image frame.

4. The method according to claim 1, wherein the first image frame is a frame corresponding to an earliest period in the set of image data.

5. The method according to claim 1, wherein the set of medical image data represents a medical image of a patient.

6. The method according to claim 1, wherein determining the position of the feature of the medical device comprises determining the position of:
a tip of a catheter;
a marker attached to an angioplasty balloon; or
a marker attached to a coronary stent.

* * * * *